United States Patent [19]

Terahara et al.

[11] Patent Number: 4,517,373
[45] Date of Patent: May 14, 1985

[54] ISOMB-530B DERIVATIVES

[75] Inventors: Akira Terahara; Minoru Tanaka, both of Hiromachi, Japan

[73] Assignee: Sankyo Company, Limited, Tokyo, Japan

[21] Appl. No.: 410,889

[22] Filed: Aug. 24, 1982

[30] Foreign Application Priority Data

Aug. 27, 1981 [JP] Japan .............................. 56-134558

[51] Int. Cl.³ .......................................... C07D 309/30
[52] U.S. Cl. .................................................... 549/292
[58] Field of Search ........................................ 549/292

[56] References Cited

FOREIGN PATENT DOCUMENTS 2049664 1/1983 United Kingdom .
2046737 1/1983 United Kingdom .

OTHER PUBLICATIONS

Nobufusa Serizawa et al., "Microbial Hydroxylation of ML-236B (Compactin) and Monacolin K (MB-530B)", The Journal of Antibiotics, vol. 36, No. 5, pp. 604-607, (May 1983).
Akiro Endo, "Monacolin K, A New Hypocholesterolemic Agent that Specifically Inhibits 3-Hydroxy-3-Methylglutaryl Coenzyme A Reductase", The Journal of Antibiotics, vol. 33, pp. 334-336, (Mar. 1980).
Akiro Endo, "Monacolin K, A New Hypocholesterolemic Agent Produced by A Monascus Species", The Journal of Antibiotics, vol. 32, pp. 852-854, (Aug. 1979).

Primary Examiner—Norma S. Milestone
Attorney, Agent, or Firm—Frishauf, Holtz, Goodman & Woodward

[57] ABSTRACT

The 1-acyloxy-6-hydroxy-IsoMB-530B lactones of the formula (I):

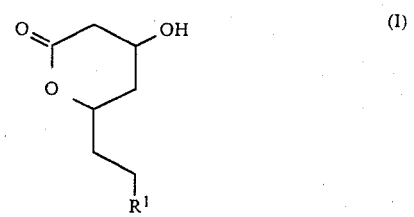

wherein $R^1$ represents a group of the formula

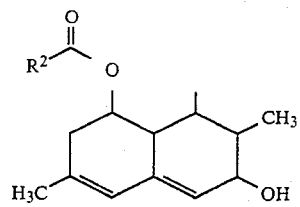

wherein $R^2$ is a $C_1$–$C_{10}$ alkyl group.

3 Claims, No Drawings

ISOMB-530B DERIVATIVES

BACKGROUND OF THE DISCLOSURE

The present invention relates to a series of new derivatives of the known compound MB-530B, to processes for their preparation and to pharmaceutical compositions containing them.

MB-530B has been disclosed in United Kingdom Patent Specifications Nos. 2,046,737 and 2,049,664, in both of which it is designated "Monacolin K," but it has also been assigned the designation "MB-530B", by which it is referred to herein. MB-530B can exist in the form of a lactone, termed "MB-530B lactone", which has the structural formula:

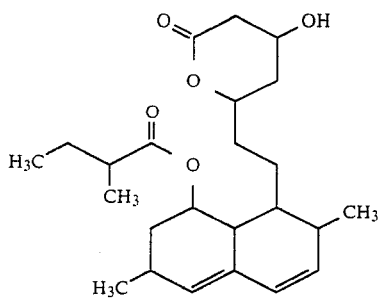

or in the form of the corresponding free hydroxy-carboxylic acid, termed "MB-530B carboxylic acid", which has the structural formula:

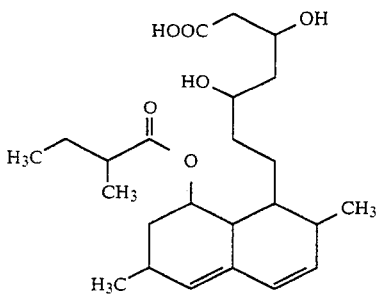

These MB-530B compounds have been isolated and purified from the metabolic products of various microorganisms, including microorganisms of the genus Monascus, especially Monascus ruber, a species of mould. They have been shown to inhibit the biosynthesis of cholesterol in enzyme systems and in systems comprising cultured cells separated from experimental animals by competing with the rate-limiting enzyme active in the biosynthesis of cholesterol, that is to say 3-hydroxy-3-methylglutaryl-coenzyme A reductase, and, as a result, they significantly reduce serum cholesterol levels in animals.

Salts and esters of MB-530B carboxylic acid, which share the activity of the parent compound, have been disclosed in United Kingdom Patent Specification No. 2,055,100.

There is also known a series of compounds which bear structural similarities to the MB-530B compounds—this series comprises the compounds known as ML-236B and derivatives thereof. ML-236B lactone, which is disclosed in U.S. Pat. No. 3,983,140, has the structural formula:

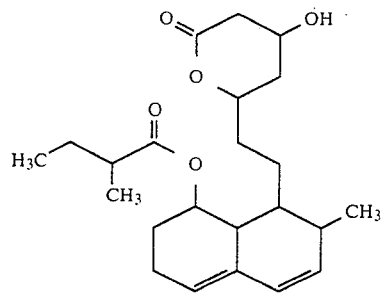

and this, of course, also forms a corresponding free hydroxycarboxylic acid. Like the MB-530B compounds, ML-236B lactone and its corresponding carboxylic acid have the ability to inhibit the biosynthesis of cholesterol.

A number of compounds structurally related to ML-236B have also been discovered and some have been found to share this ability to inhibit the biosynthesis of cholesterol. Of the ML-236B derivatives which have been discovered, the most relevant form the subject of co-pending U.S. patent application Ser. No. 270,846, filed 5th June 1981 which issued as U.S. Pat. No. 4,346,227. In the lactone form, these compounds may be represented by the structural formula:

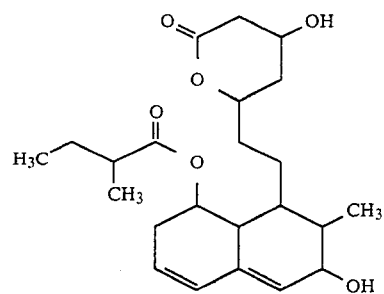

and have been named "IsoM-4 lactone" or "IsoM-4' lactone", depending upon the particular configuration of the various asymmetric carbon atoms present in the molecule. The corresponding IsoM-4 carboxylic acid and IsoM-4' carboxylic acid are also disclosed and these compounds were all found to have the ability to inhibit the biosynthesis of cholesterol.

We have now discovered a new series of compounds, which are derivatives of MB-530B, and which, whilst having an ability to inhibit the biosynthesis of cholesterol which is generally at least comparable with that of the known compounds, are metabolised with much greater difficulty after administration than are MB-530B and ML-236B. The compounds of the invention are thus less readily deactivated in vivo and hence have more persistent activity, with attendant advantages well recognised in the art.

BRIEF SUMMARY OF INVENTION

The compounds of the present invention are the lactones of formula (I):

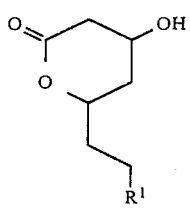

in which R[1] represents a group of formula

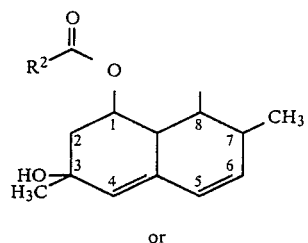

or

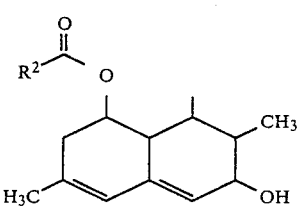

(wherein R[2] represents a $C_1$–$C_{10}$ alkyl group) and the corresponding free hydroxy-carboxylic acids, which may be represented by the structural formula (II):

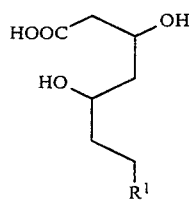

(II)

ps (in which R[1] is as defined above) and salts and esters of said acids.

The compounds of the present invention may be prepared by the enzymatic hydroxylation of MB-530B lactone, MB-530B carboxylic acid or a salt or ester of said carboxylic acid or a corresponding compound in which the 2-methylbutyryloxy group at the 1-position has been replaced by another acyloxy group. (these compounds are hereinafter collectively referred to as "the MB-530B compounds"). The MB-530B compounds are thus those compounds of formulae (VI) and (VII):

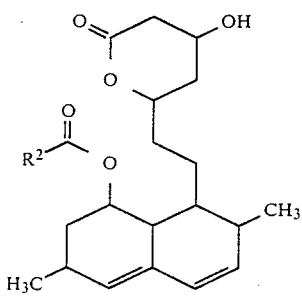

(VI)

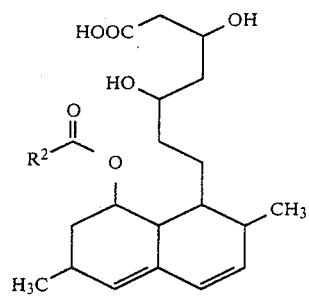

(VII)

(in which R[2] is as defined above) and salts and esters of compound (VII).

The invention also provides a pharmaceutical composition for the reduction of blood cholesterol levels, comprising an active ingredient in admixture with a pharmaceutically acceptable carrier or diluent, wherein the active ingredient is at least one compound selected from the compounds of formula (I), the corresponding free hydroxy-carboxylic acids and salts and esters of said acids.

DETAILED DESCRIPTION OF INVENTION

The compound of formula (I) in which R[1] represents a group of formula:

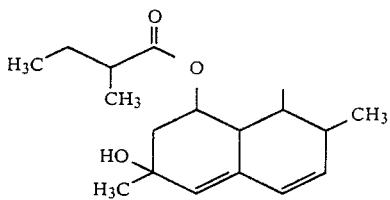

that is to say the compound of formula (Ia):

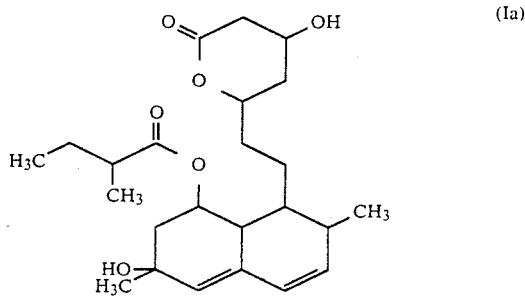

(Ia)

is hereinafter called "3-hydroxy-MB-530B lactone", whilst the corresponding free hydroxy-carboxylic acid is called "3-hydroxy-MB-530B carboxylic acid" and the salts and esters are named appropriately as derivatives of the acid.

Similarly, the compound of formula (I) in which R[1] represents a group of formula:

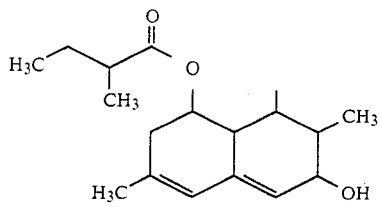

that is to say the compound of formula (Ib):

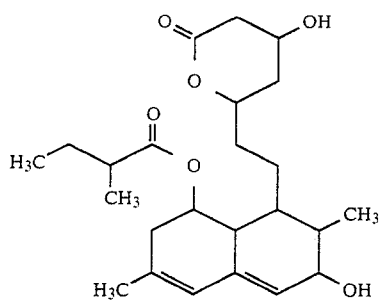

is called "6-hydroxy-IsoMB-530B lactone", whilst the corresponding free hydroxy-carboxylic acid is called "6-hydroxy-IsoMB-530B carboxylic acid" and the corresponding salts and esters are named appropriately as derivatives of the carboxylic acid.

Compounds of formula (I) in which $R^2$ represents a group other than the sec-butyl group are named by adding the name of the acyloxy group $R^2COO-$, which is at the 1-position in the compound, as a prefix to the name of the corresponding compound in which $R^2$ represents a sec-butyl group. For example, a compound of formula (Ia) in which the 2-methylbutyryloxy group at the 1-position ($R^2$=sec-butyl) has been replaced by an acetoxy group ($R^2$=methyl), i.e. a compound of formula (Ic):

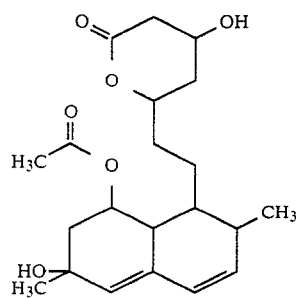

is called "1-acetoxy-3-hydroxy-MB-530B lactone", whilst a compound of formula (Ib) in which the 2-methylbutyryloxy group at the 1-position ($R^2$=sec-butyl) has been replaced by a valeryloxy group ($R^2$=n-butyl), i.e. a compound of formula (Id):

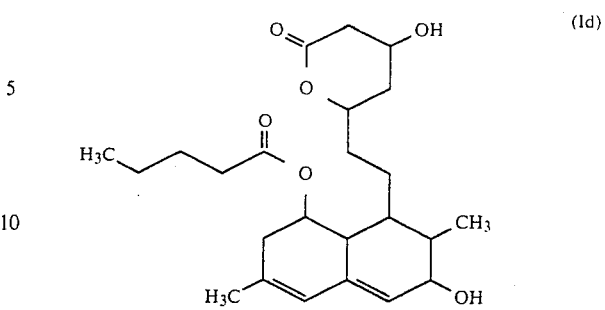

is called "1-valeryloxy-6-hydroxy-IsoMB-530B lactone".

$R^2$ represents an alkyl group having from 1 to 10 carbon atoms and may be a straight or branched chain group. Examples of the groups represented by $R^2$ include the methyl, ethyl, propyl, butyl, pentyl, hexyl, heptyl, octyl, nonyl, decyl, isopropyl, isobutyl, sec-butyl, t-butyl, isopentyl, neopentyl, t-pentyl, isohexyl, 1-ethylpropyl, 1-methylpentyl, 1-ethyl-1-methylpropyl, 1,1-dimethylpentyl, 1,2-dimethylpentyl, 1-methylhexyl, 1,1-dimethylhexyl, 1-methylheptyl, 1,1-dimethylheptyl, 1-methyloctyl, 1,1-dimethyloctyl and 1-methylnonyl groups. Especially preferred is the sec-butyl group.

The salts of the present invention may be metal salts, ammonium salts or salts with organic amines or amino acids.

Metal salts of the compounds may be represented by formula (III):

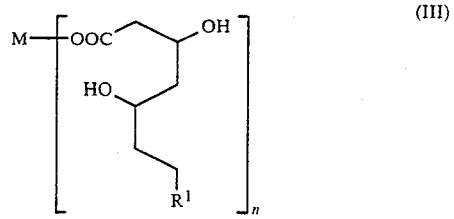

(in which $R^1$ is as defined above, M represents a metal atom and n represents the valency of the metal atom M). Examples of metals which may be represented by M in these salts include: alkali metals, such as sodium or potassium; alkaline earth metals, such as calcium; and other metals, such as magnesium, aluminium, iron, zinc, copper, nickel or cobalt. Of these metals, the alkali metals, alkaline earth metals, magnesium and aluminium are preferred, sodium, potassium, calcium and aluminium being most preferred.

The ammonium, organic amine and amino acid salts of the compounds of the invention may be represented by formula (IV):

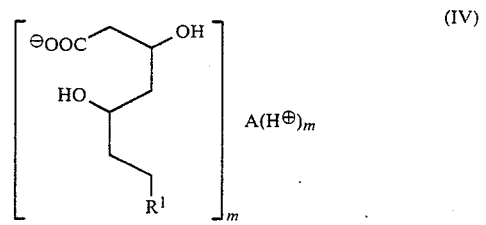

(in which $R^1$ is as defined above, A represents ammonia, an amino acid or an organic amine, and m is an integer). The integer represented by m is preferably 1, that is to say that, where A represents an amine or amino acid, the amine or amino acid is preferably monoacidic.

Examples of amino acids which may be represented by A in the above formula (IV) include such basic amino acids as arginine, lysine, histidine, 2,4-diaminobutyric acid and ornithine.

When A represents an organic amine, it is preferably a monoamine and may be an aliphatic, aromatic, alicyclic, heterocyclic or carbohydrate monoamine. Examples include: primary alkylamines, such as octylamine, t-octylamine or 2-ethylhexylamine; primary, secondary and tertiary $C_7$ or $C_8$ aralkylamines, such as benzylamine, α-methylbenzylamine, phenethylamine, dibenzylamine, N-methylbenzylamine, N,N-dimethylbenzylamine, N,N-diethylbenzylamine, N-ethyl-N-methylbenzylamine or tribenzylamine; primary, secondary or tertiary $C_5$–$C_7$ saturated alicyclic amines, such as cyclopentylamine, cyclohexylamine, cycloheptylamine, N-methylcyclopentylamine, N-ethylcyclohexylamine, N-ethylcycloheptylamine, dicyclohexylamine, N,N-dimethylcyclopentylamine, N,N-dimethylcyclohexylamine or N,N-diethylcycloheptylamine; 5 or 6 membered heterocyclic amines having a single nitrogen atom as the hetero atom, such as pyrrolidine, N-methylpyrrolidine, piperidine or N-methylpiperidine; morpholine; $C_1$–$C_3$ alkyl esters of aliphatic or aromatic amino acids, such as leucine methyl ester, diethyl glutamate, phenylglycine ethyl ester, β-phenylalanine propyl ester or β-phenylalanine methyl ester; and amine derivatives of carbohydrates, such as glucosamine.

Where the amino acids and amines mentioned above can exist in the form of stereoisomers or optical isomers, it is possible to use any of the isomers or mixtures thereof.

Preferred amines are t-octylamine, benzylamine, dibenzylamine, N,N-dimethylbenzylamine, cyclohexylamine, dicyclohexylamine, N,N-dimethylcyclohexylamine, N-methylpyrrolidine, morpholine, L-leucine alkyl esters, dialkyl L-glutamates, D-phenylglycine alkyl esters and D-glucosamine; of which the most preferred amines are t-octylamine, dibenzylamine, dicyclohexylamine, morpholine, D-phenylglycine alkyl esters and D-glycosamine.

Of the salts, we especially prefer to employ the alkali metal salts, most preferably the sodium or potassium salts.

Esters of the compounds of the invention may be represented by formula (V):

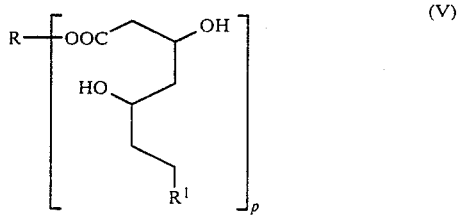

(in which $R^1$ is as defined above, R represents the alcoholic moiety of an ester and p represents the valency of R).

Where p represents 1, R preferably represents an alkyl group, an unsubstituted benzyl group, a substituted benzyl group having at least one substituent selected from alkyl groups, alkoxy groups and halogen atoms, an unsubstituted phenacyl group or a substituted phenacyl group having at least one substituent selected from alkyl groups, alkoxy groups and halogen atoms.

Where R represents an alkyl group, this may be a straight or branched chain group and preferably has from 1 to 6 carbon atoms. Examples of such a group include the methyl, ethyl, propyl, isopropyl, butyl, pentyl and hexyl groups.

Where R represents a benzyl group, this may be unsubstituted or substituted, the substituents preferably being $C_1$ or $C_2$ alkyl or alkoxy groups or halogen atoms. One or more, preferably one, substituents are possible and, if there is more than one substituent, these may be the same or different. Examples of such benzyl groups include the benzyl, 2-methylbenzyl, 3-methylbenzyl, 4-methylbenzyl, 2-ethylbenzyl, 3-ethylbenzyl, 4-ethylbenzyl, 2-methoxybenzyl, 3-methoxybenzyl, 4-methoxybenzyl, 2-ethoxybenzyl, 3-ethoxybenzyl, 4-ethoxybenzyl, 2-chlorobenzyl, 3-chlorobenzyl, 4-chlorobenzyl, 2-bromobenzyl, 3-bromobenzyl and 4-bromobenzyl groups.

R may represent an unsubstituted or substituted phenacyl group, in which the substituents are preferably $C_1$ or $C_2$ alkyl or alkoxy groups or halogen atoms. One or more, preferably one, substituents are possible and, where there is more than one substituent, these may be the same or different. Examples of such phenacyl groups include the phenacyl, 2-methylphenacyl, 3-methylphenacyl, 4-methylphenacyl, 2-ethylphenacyl, 3-ethylphenacyl, 4-ethylphenacyl, 2-methoxyphenacyl, 3-methoxyphenacyl, 4-methoxyphenacyl, 2-ethoxyphenacyl, 3-ethoxyphenacyl, 4-ethoxyphenacyl, 2-chlorophenacyl, 3-chlorophenacyl, 4-chlorophenacyl, 2-bromophenacyl, 3-bromophenacyl and 4-bromophenacyl groups.

Where p is 2, R represents a bivalent alcoholic moiety, preferably a $C_2$–$C_6$ alkylene or alkylidene group, for example, an ethylene, ethylidene, propylene, propylidene, trimethylene, tetramethylene, butylidene, pentamethylene or pentylidene group, as well as such groups having one or more substituents, e.g. hydroxy groups, halogen atoms, or trifluoromethyl groups.

Where p is 3, R represents a trivalent alcoholic moiety and it is preferably a saturated aliphatic hydrocarbon group having from 2 to 6 carbon atoms and optionally one or more substituents, e.g. hydroxy groups, halogen atoms or trifluoromethyl groups.

We prefer that p should be 1 and that R should represent an alkyl group (most preferably methyl, ethyl, propyl, isopropyl, butyl, isobutyl or hexyl), an optionally substituted benzyl group (most preferably benzyl, 4-methylbenzyl, 4-methoxybenzyl or 4-chlorobenzyl) or an optionally substituted phenacyl group (most preferably phenacyl, 4-methylpenacyl, 4-methoxyphenacyl or 4-bromophenacyl).

The most preferred groups represented by R are the methyl, ethyl, propyl, isopropyl, butyl and isobutyl groups.

The compounds of the invention have been found to inhibit cholesterol biosynthesis in the liver and thus may be used for the treatment of hypercholesteraemia or the prevention of arteriosclerosis, in the same way as are the compounds disclosed in United Kingdom Patent Specifications Nos. 2,046,737, 2,049,664 and 2,055,100.

The inhibitory activities of certain of the compounds of the invention, in terms of the concentration in μg/ml required to inhibit cholesterol biosynthesis by 50%

[measured by the method described in the Journal of Biological Chemistry, 234, 2835 (1959)], are as follows:
Methyl 3-hydroxy-MB-530B carboxylate: 0.0005
6-hydroxy-IsoMB-530B lactone: 0.013
Sodium 6-hydroxy-IsoMB-530B carboxylate: 0.0029

For comparison, the value for MB-530B lactone is 0.002 μg/ml which is comparable with the levels achieved by the compounds of the invention, but, as previously noted, by virtue of their resistance to in vivo degradation, the activity of the compounds of the invention is far more persistent.

The compounds of the invention may be administered by any conventional means, for example parenterally (e.g. by subcutaneous, intravenous or intramuscular injection) or orally (e.g. in the form of tablets, capsules, powders or granules). The adult daily dose will, of course, vary depending upon the age, body weight and condition of the patient, as well as upon the route and times of administration, but, in general, the compounds of the invention are preferably administered in an amount of from 0.2 to 200 mg/day for adults in a single dose or in divided doses, preferably 3 or 4 times per day.

The enzymatic hydroxylation process of the present invention is preferably effected by contacting the MB-530B compound with a microorganism of the genus Syncephalastrum, Mucor, Rhizopus, Zygorynchus, Circinella, Actinomucor, Gongronella, Phycomyces, Streptomyces, Absidia, Cunninghamella, Mortierella, Pycnoporus or Rhizoctonia which is capable of converting the MB-530B compound to the desired compound of the invention or by contacting said MB-530B compound with an enzyme-containing extract from said microorganism, and then separating the compound of the invention from the culture medium or the reaction mixture.

Any microorganism capable of converting the MB-530B compound to the compound of the invention may be employed, although microorganisms of the genera Syncephalastrum, Mucor, Rhizopus, Zygorynchus, Circinella, Actinomucor, Gongronolla, Phycomyces, Streptomyces, Absidia, Cunninghamella or Mortierella (all of which are members of the Zygomycetes) or Pycnoporus (formerly named Trametes) or Rhizoctonia are preferred.

Of the microorganisms of the above genera, we prefer to employ the following species:
*Absidia coerulea*
*Cunninghamella echinulata*
*Syncephalastrum racemosum*
*Streptomyces roseochromogenus*
*Mucor hiemalis f. hiemalis*
*Mucor bacilliformis*
*Mucor circinelloides f. circinelloides*
*Mucor hiemalis f. corticolus*
*Mucor dimorphosporus*
*Mucor fragilis*
*Mucor genevensis*
*Mucor globosus*
*Mucor circinelloides f. griseocyanus*
*Mucor heterosporus*
*Mucor spinescens*
*Rhizopus chinensis*
*Rhizopus circinans*
*Rhizopus arrhizus*
*Zygorynchus moelleri*
*Circinella muscae*
*Circinella rigida*
*Circinella umbellata*
*Actinomucor elegans*
*Phycomyces blakesleeanus*
*Mortierella isabellina*
*Gongronella butleri*
*Pycnoporus coccineus*
*Rhizoctonia solani*
*Syncephalastrum nigricans*
*Absidia glauca var. paradoxa.*

Amongst strains of the above species, the following are particularly preferred:
*Absidia coerulea* IFO-4423
*Cunninghamella echinulata* IFO-4445
*Cunninghamella echinulata* IFO-4444
*Cunninghamella echinulata* ATCC-9244
*Syncephalastrum racemosum* IFO-4814
*Streptomyces roseochromogenus* NRRL-1233
*Mucor hiemalis f. hiemalis* IFO-5834
*Mucor hiemalis f. hiemalis* IFO-5303
*Mucor hiemalis f. hiemalis* IFO-8567
*Mucor hiemalis f. hiemalis* IFO-8449
*Mucor hiemalis f. hiemalis* IFO-8448
*Mucor hiemalis f. hiemalis* IFO-8565
*Mucor hiemalis f. hiemalis* CBS-117.08
*Mucor hiemalis f. hiemalis* CBS-109.19
*Mucor hiemalis f. hiemalis* CBS-200.28
*Mucor hiemalis f. hiemalis* CBS-242.35
*Mucor hiemalis f. hiemalis* CBS-110.19
*Mucor hiemalis f. hiemalis* CBS-201.65
*Mucor bacilliformis* NRRL-2346
*Mucor circinelloides f. circinelloides* IFO-4554
*Mucor circinelloides f. circinelloides* IFO-5775
*Mucor hiemalis f. corticolus* FERM-5913
*Mucor dimorphosporus* IFO-4556
*Mucor fragilis* CBS-236.35
*Mucor genevensis* IFO-4585
*Mucor globosus* FERM-5915
*Mucor circinelloides f. griseocyanus* IFO-4563
*Mucor heterosporus* NRRL-3154
*Mucor spinescens* IAM-6071
*Rhizopus chinensis* IFO-4772
*Rhizopus circinans* ATCC-1225
*Rhizopus arrhizus* ATCC-11145
*Zygorynchus moelleri* IFO-4833
*Circinella muscae* IFO-4457
*Circinella rigida* NRRL-2341
*Circinella umbellata* NRRL-1713
*Circinella umbellata* IFO-4452
*Circinella umbellata* IFO-5842
*Phycomyces blakesleeanus* FERM-5914
*Mortierella isabellina* IFO-6739
*Gongronella butleri* IFO-8080
*Pycnoporus coccineus* FERM-5916
*Rhizoctonia solani* FERM-5917
*Syncephalastrum nigricans* FERM-6041
*Syncephalastrum nigricans* FERM-6042
*Syncephalastrum nigricans* FERM-6043
*Absidia glauca var. paradoxa* IFO-4431
*Actinomucor elegans* ATCC-6476.

Most preferred are strains of *Mucor hiemalis f. hiemalis*, especially *Mucor hiemalis f. hiemalis* IFO-5834.

The microorganisms listed above are available from International Culture Collections, as indicated by the codes appended to their accession numbers, which codes have the following meanings.
IFO=Institute for Fermentation, Osaka, Japan
NRRL=Agricultural Research Culture Collection, Illinois, USA CBS=Centraal Bureau voor Schimmelcultures, Netherlands IAM=Institute of Applied Microbiology, Tokyo, Japan ATCC=American Type Culture Collection, Maryland, USA FERM=The Fermentation Research Institute, Agency of Industrial Science and Technology, Ministry of International Trade and Industry, Japan.

Conversion of the MB-530B compound to the compound of the invention may be achieved by contacting the complete cellular microorganism, which may be in a culture or may be a resting cellular system, or, in some cases, a cell-free extract from the microorganism with the MB-530B compound. The form of the compound produced will depend upon the culture conditions and the form of the microorganism employed as well as, to some extent, on the nature of the starting material. Thus, for example, if the complete cellular microorganism is cultivated in the presence of the MB-530B compound, the product may be the carboxylic acid, the lactone, the ester (especially alkyl ester) or the salt (especially alkali metal salt), depending upon the culture conditions, particularly the pH value. On the other hand, if the MB-530B compound is simply contacted with the resting cellular system or with a cell-free extract, the compound of the invention is most frequently obtained in the form of the alkali metal salt. In all cases, the compound is normally obtained in the form of a mixture of the 3-hydroxy-MB-530B compound and the 6-hydroxy-IsoMB-530B compound.

The progress of the conversion reaction may be determined by assaying samples of the reaction mixture during the course of the reaction to determine the degree of conversion.

Where the microorganisms are to be cultivated in the presence of the MB-530B compound to produce the compounds of the invention, the culture conditions and culture media employed will be chosen having regard to the requirements of the particular microorganism to be cultivated. Since the species of microorganism proposed for use in the process of the present invention are all known, culture conditions and culture media for use with these microorganims are also known.

The compounds of the invention may be separated from the reaction mixture by conventional means, for example by filtering off microbial cells (if necessary) and then subjecting the remaining mixture to any combination of thin layer chromatography, column chromatography or high performance liquid chromatography. The two isomeric forms of the compounds of the invention may, if desired, be separated from each other in the course of one or more of these chromatographic purification steps or they may be separated as a mixture.

Where the enzymatic hydroxylation process of the present invention produces the carboxylic acid or lactone, these may be converted by conventional chemical reactions to the corresponding salts or esters. For example, metal salts [that is to say compounds of formula (III)] and amino acid salts [that is to say compounds of formula (IV) in which A represents an amino acid] may be prepared by the method described in United Kingdom Patent Specification No. 1,555,831 for the preparation of salts of ML-236B carboxylic acid.

Amine salts may be prepared by reacting an alkali metal carboxylate of the chosen compound (for example, the sodium carboxylate) with a mineral acid (e.g. hydrochloric acid) salt of ammonia or of an organic amine in a suitable solvent. The nature of the solvent is not critical, provided that it has no adverse effect upon the reaction, aqueous solvents being preferred. Examples of such solvents include water itself and mixtures of water with one or more organic solvents, such as alcohols (e.g. methanol or ethanol) or ketones (e.g. acetone). The amount of amine salt is preferably equimolar or a slight molar excess, with respect to the metal carboxylate, e.g. a molar ratio amine salt:metal carboxylate of from 1:1 to 1.2:1. The reaction is preferably effected at a pH value of from 7.0 to 8.5 and at a temperature of ambient or below, e.g. from 0° C. to 10° C., more preferably from 5° C. to 10° C. After the reaction, the resulting salt may be separated from the reaction mixture by extraction with a suitable solvent, such as ethyl acetate.

Esters, that is to say compounds of formula (V), may be prepared by esterification of the lactone or carboxylic acid or of a corresponding salt (preferably an alkali metal salt), for example as described in United Kingdom Patent Specification No. 1,555,831 in relation to the preparation of esters of ML-236B carboxylic acid, i.e. either by reaction of the starting material with an alcohol in the presence of a suitable catalyst or by reaction of this material with a diazo compound, preferably diazomethane or a C-substituted diazomethane.

It is also possible, by appropriate adjustment of pH conditions, to convert the carboxylic acid to its corresponding lactone and vice versa.

Also, by appropriate chemical reactions, it is possible to convert esters, i.e. compounds of formula (V) to salts, e.g. by an appropriate combination of the above-described reactions.

The conversion reactions described above may be carried out after the starting material has been isolated and purified from the culture medium or the reaction mixture or they may be carried out prior to or in the course of the separation procedure.

Of the starting materials, MB-530B lactone and MB-530B carboxylic acid may be prepared as described in United Kingdom Patent Specifications No. 2,046,737 and No. 2,049,664, whilst salts and esters of MB-530B carboxylic acid may be prepared as described in United Kingdom Patent Specification No. 2,055,100. Starting materials in which $R^2$ represents a group other than the sec-butyl group may be prepared by a transacylation reaction commencing with the corresponding MB-530B compound in which $R^2$ represents a sec-butyl group or, and more preferably, they may be prepared from MB-530A, as described in United Kingdom Patent Specification No. 2,073,193, e.g. by the following methods:

Method 1

MB-530A is reacted with an acid chloride or acid anhydride appropriate to the group of formula $R^2COO-$ which it is desired to introduce at the 1-position. The reaction is preferably carried out in the presence of a base (which acts as an acid-binding agent), preferably an organic amine, such as pyridine, triethylamine, N,N-dimethylaminopyridine, N-methylpyrrolidine or N-methylmorpholine. The reaction is preferably carried out in the presence of a solvent and the nature of this solvent is not critical, provided that it does not adversely affect the reaction. Suitable solvents include chloroform, methylene chloride and diethyl ether. In some cases, it is possible to carry out the reaction using as solvent an excess of one of the reagents or of the base. The reaction will take place over a wide range of temperatures, although, in order to control the reaction properly, a relatively low temperature is normally preferred, for example from −20° C. to room temperature, more preferably from −20° C. to 0° C. However, higher temperatures may also be employed, if desired.

Method 2

A carboxylic acid is treated with a chlorocarbonate ester or with a sulphonic acid chloride in the presence of a base, for example one of the organic amines mentioned above, to prepare a mixed acid anhydride and this is, in turn, reacted with MB-530A. The reaction is preferably effected in the presence of a solvent, the nature of which is not critical, provided that it has no adverse effect upon the reaction. Suitable solvents include, for example, diethyl ether, benzene, chloroform and methylene chloride. The reaction will take place over a wide range of temperatures, for example from −20° C. to ambient temperature, preferably from −20° C. to 0° C.

Method 3

MB-530A is reacted with a carboxylic acid and a diazoalkyl dicarboxylate in the presence of, for example, dicyclohexylcarbodiimide, triphenylphosphine or dimethylphosphorus amide. The reaction is preferably effected in the presence of a solvent, the nature of which is not critical, provided that it has no adverse effect upon the reaction. Suitable solvents include chloroform, methylene chloride, benzene and diethyl ether and the reaction may be carried out over a wide temperature range.

Each of the above reactions will normally be complete within a period of from 30 minutes to 5 hours, although the precise time required for the reaction will depend upon the reagents and the reaction temperature. After completion of the reaction, the desired product may be separated from the reaction mixture by conventional means, e.g. by evaporating the solvent from a solution containing the desired product (which solution may be simply the reaction mixture or may be a solution obtained by extracting the reaction mixture with an organic solvent), optionally after washing and drying the solution, after which the product may be purified by conventional means, for example by column chromatography, thin layer chromatography, recrystallisation or any combination thereof.

It should be noted that the numbering system employed in defining the compounds described in United Kingdom Patent Specification No. 2,073,193 differs from that employed in the present invention. For the purposes of the present invention, it should be noted that the "8'-position" defined in United Kingdom Patent Specification No. 2,073,193 is equivalent to the 1-position referred to in the present specification. Accordingly, compounds having names of the type "MB-530A 8'-acylate" in United Kingdom Patent Specification No. 2,073,193 are referred to herein as "MB-530A 1-acylate".

The invention is further illustrated by the following Examples.

EXAMPLE 1

3-Hydroxy-MB-530B carboxylic acid, 6-hydroxy-IsoMB-530B carboxylic acid and their methyl esters Twenty 500 ml Erlenmeyer flasks, each containing 100 ml of a medium having the composition described below, were inoculated with spores of *Mucor hiemalis f. hiemalis* IFO-5834. The flasks were subjected to shaking culture at 26° C. and 220 revolutions per minute (r.p.m.) for 4 days. At the end of this time, MB-530B lactone was added to each of the flasks to a final concentration of 0.05% w/v. Cultivation was continued at 26° C. and 220 r.p.m. for a further 6 days.

The composition of the medium was (percentages are w/v):

Glucose: 1.0%
Peptone: 0.2%
Meat extract: 0.1%
Yeast extract: 0.1%
Corn steep liquor: 0.3%
Tap water: the balance (pH was not adjusted)

After completion of the cultivation, the reaction liquor was filtered and the resulting 1.9 liters of filtrate were absorbed on a column of Diaion HP-20 (a product of Mitsubishi Chemical Industries Co.). The column was eluted with 70% v/v aqueous methanol and then the solvent was distilled from the eluate. The residue was adjusted with trifluoroacetic acid to pH 3.0 and then extracted twice, each time with 1 liter of ethyl acetate, to give extracts containing 3-hydroxy-MB-530B carboxylic acid and 6-hydroxy-IsoMB-530B carboxylic acid. A sample of this fraction was subjected to thin layer chromatography using a silica gel Art 5715 plate (manufactured by Merck & Co.) and using a 50:50:3 by volume mixture of benzene, acetone and acetic acid as the developing solvent. The two acids had an identical Rf value of 0.47.

To the remainder of the fraction was added immediately a stoichiometric excess of an ethereal solution of diazomethane. The mixture was then left to stand for 30 minutes, after which it was washed with a saturated aqueous solution of sodium chloride and then evaporated to dryness under reduced pressure. The resulting residue was then subjected to high-performance liquid chromatography through a $\mu$Bondapak $C_{18}$ (a product of Waters Co., U.S.A) column eluted with 53% v/v aqueous methanol. The first fractions to be eluted contained methyl 3-hydroxy-MB-530B carboxylate, whilst subsequent fractions contained methyl 6-hydroxy-IsoMB-530B carboxylate.

The fractions were separately collected and purified to give 180 mg of methyl 3-hydroxy-MB-530B carboxylate and 170 mg of methyl 6-hydroxy-IsoMB-530B carboxylate, having the following characteristics:

Methyl 3-hydroxy-MB-530B carboxylate

1—Nuclear Magnetic Resonance Spectrum, measured at 90 MHz in deuterochloroform, using tetramethylsilane as the internal standard, δppm:
3.72 (3H, singlet);
4.28 (1H, quintet);
5.45 (2H, multiplet);
5.93 (1H, quartet);
6.01 (1H, doublet).

2—Ultraviolet Absorption Spectrum (methanol) $\lambda_{max}$ nm: 229, 236, 244.5.

3—Infrared Absorption Spectrum (thin film) $\nu_{max}$ $cm^{-1}$: 3410, 2975, 1730.

4—Elemental analysis: Calculated for $C_{25}H_{40}O_7$: C, 66.34%; H, 8.91%. Found: C, 66.30%; H, 8.02%.

Methyl 6-hydroxy-IsoMB-530B carboxylate

1—Nuclear Magnetic Resonance Spectrum, measured at 90 MHz in deuteroacetone, using tetramethylsilane as the internal standard, δppm:
3.70 (3H, singlet);
4.22 (1H, multiplet);
5.42 (1H, multiplet);
5.57 (1H, multiplet);
5.92 (1H, doublet).

2—Ultraviolet Absorption Spectrum (methanol) $\lambda_{max}$ nm: 238.4.

3—Infrared Absorption Spectrum (thin film) $\nu_{max}$ cm$^{-1}$: 3400, 2960, 1732.

4—Elemental analysis: Calculated for $C_{25}H_{40}O_7$: C, 66.34%; H, 8.91%. Found: C, 66.28%; H, 8.11%.

EXAMPLE 2

The procedure described in Example 1 was repeated, except that the microorganism employed was as shown in the following Table, which also shows the yields of product ("Me 3-OH-MB-530B"=methyl 3-hydroxy-MB-530B carboxylate and "Me 6-OH-IsoMB-530B"=methyl 6-hydroxy-IsoMB-530B carboxylate):

TABLE

| Microorganism | Yield (mg) | |
| --- | --- | --- |
| | Me 3-OH—MB-530B | Me 6-OH—IsoMB-530B |
| Syncephalastrum nigricans FERM - 6041 | 18 | 12 |
| Rhizopus chinensis IFO - 4772 | 20 | 7 |
| Zygorynchus moelleri IFO - 4833 | 7 | 14 |
| Circinella muscae IFO - 4457 | 5.5 | 11.2 |
| Actinomucor elegans ATCC - 6476 | 14 | 2 |
| Gongronella butleri IFO - 8080 | 8 | 9 |
| Phycomyces blakesleeanus FERM - 5914 | 13 | 11 |
| Streptomyces roseochromogenus NRRL - 1233 | 3.3 | 7.2 |
| Absidia coerulea IFO - 4423 | 4.2 | 5.5 |
| Cunninghamella echinulata IFO - 4445 | 8.2 | 13.2 |
| Mortierella isabellina IFO - 6739 | 11.2 | 8.2 |
| Pycnoporus coccineus FERM - 5916 | 12.1 | 10.2 |
| Rhizoctonia solani FERM - 5917 | 11.0 | 12.1 |

EXAMPLE 3

6-hydroxy-IsoMB-530B lactone

The procedure described in Example 1 was repeated to give 1.9 liters of reaction liquor. The pH value of this liquor was adjusted, by the addition of trifluoroacetic acid, to 3.0, and then the liquor was extracted three times, each time with 1 liter of ethyl acetate. The combined extracts were washed with a saturated aqueous solution of sodium chloride and then dried over sodium sulphate, after which a catalytic amount of trifluoroacetic acid was added. The resulting mixture was washed with a 5% w/v aqueous solution of sodium bicarbonate, dried over anhydrous sodium sulphate and then evaporated to dryness under reduced pressure. The resulting residue was purified by chromatography through a Lobar column (Merck Si60, size A) eluted with ethyl acetate, to give 212 mg of the desired 6-hydroxy-IsoMB-530B lactone having the following physical properties:

1—Nuclear Magnetic Resonance Spectrum, measured at 90 MHz in deuteroacetone, using tetramethylsilane as the internal standard, δppm:
3.94 (1H, doublet);
4.35 (1H, multiplet);
4.66 (1H, multiplet);
5.45 (1H, multiplet);
5.62 (1H, doublet);
5.91 (1H, singlet).

2—Ultraviolet Absorption Spectrum (methanol) $\lambda_{max}$ nm 238.4

3—Infrared Absorption Spectrum (KBr) $\nu_{max}$ cm$^{-1}$: 3450, 1730.

4—Mass Spectrum: m/e: 420 (M$^+$).

5—Elemental analysis: Calculated for $C_{24}H_{36}O_6$: C, 68.54%; H, 8.63%. Found: C, 68.33%; H, 8.81%.

EXAMPLE 4

Sodium 3-hydroxy-MB-530B carboxylate 100 mg of methyl 3-hydroxy-MB-530B carboxylate were dissolved in a 0.1N aqueous solution of sodium hydroxide, after which the solution was stirred at 30° C. for 1 hour. The solution was then washed with chloroform and freeze-dried to give 90 mg of sodium 3-hydroxy-MB-530B carboxylate, having the following characteristics:

1—Nuclear Magnetic Resonance Spectrum, measured at 90 MHz in D$_2$O, using sodium 2,2-dimethyl-2-silapentane-5-sulphonate as the internal standard, δppm:
5.40 (2H, multiplet);
5.89 (1H, quartet);
6.00 (1H, doublet).

2—Ultraviolet Absorption Spectrum (H$_2$O) $\lambda_{max}$ nm: 229, 236, 245.

3—Infrared Absorption Spectrum (KBr) $\nu_{max}$ cm$^{-1}$: 3400, 2900, 1580.

4—Elemental analysis: Calculated for $C_{24}H_{37}O_7Na$: C, 62.59%; H, 8.10%. Found: C, 62.37%; H, 8.21%.

EXAMPLE 5

Sodium 6-hydroxy-IsoMB-530B carboxylate 100 mg of 6-hydroxy-IsoMB-530B lactone were dissolved in a small amount of acetone, after which an equivalent amount of a 0.2N aqueous solution of sodium hydroxide was added to the solution. The resulting mixture was stirred at room temperature and then freeze-dried, to give 106 mg of the desired sodium 6-hydroxy-IsoMB-530B carboxylate, having the following characteristics:

1—Nuclear Magnetic Resonance Spectrum, measured at 90 MHz in D$_2$O, using sodium 2,2-dimethyl-2-silapentane-5-sulphonate as the internal standard, δppm:
3.78 (1H, multiplet);
4.01 (1H, multiplet);
4.13 (1H, multiplet);
5.49 (1H, multiplet);
5.62 (1H, multiplet);
6.02 (1H, broad singlet).

2—Ultraviolet Absorption Spectrum (H$_2$O) $\lambda_{max}$ nm: 238.

3—Infrared Absorption Spectrum (KBr) $\nu_{max}$ cm$^{-1}$: 3400–2900, 1575.

4—Elemental analysis: Calculated for $C_{24}H_{37}O_7Na$: C, 62.59%; H, 8.10%. Found: C, 62.28%; H, 8.31%.

EXAMPLE 6

Methyl 3-hydroxy-MB-530B carboxylate and methyl 6-hydroxy-IsoMB-530B carboxylate Twenty 500 ml Erlenmeyer flasks, each containing 100 ml of a medium having the composition described in Example 1, were inoculated with spores of *Mucor hiemalis f. hiemalis* IFO-5834. The flasks were then subjected to shaking culture at 26° C. and 220 r.p.m. for 4 days. At the end of this time, sodium MB-530B carboxylate was then added to each of the flasks to a final concentration of 0.05% w/v. Cultivation was continued at 26° C. and 220 r.p.m. for a further 6 days.

After completion of the cultivation, the reaction liquor was treated as described in Example 1, to give 80 mg of methyl 3-hydroxy-MB-530B carboxylate and 90 mg of methyl 6-hydroxy-IsoMB-530B carboxylate. The characteristics of both products agreed with those of the products obtained as described in Example 1.

EXAMPLE 7

6-Hydroxy-IsoMB-530B lactone

The conversion reaction described in Example 6 was repeated, to give a reaction liquor, which was then treated as described in Example 3, to give 97 mg of the desired 6-hydroxy-IsoMB-530B lactone, whose characteristics agreed with those of the product obtained as described in Example 3.

EXAMPLE 8

The procedure described in Example 3 was repeated, except that the MB-530B was replaced by the appropriate MB-530A 1-acylate, to give the following compounds (nuclear magnetic resonance spectra were measured at 90 MHz in deuterochloroform, using tetramethylsilane as the internal standard):

1-(2,2-Dimethylbutyryloxy)-6-hydroxy-IsoMB-530B lactone

Nuclear Magnetic Resonance Spectrum $\delta$ppm:
 0.82 (3H, triplet);
 0.85 (3H, doublet);
 1.12 (6H, singlet);
 1.70 (3H, singlet);
 3.92 (1H, doublet);
 4.32 (1H, multiplet);
 4.63 (1H, multiplet);
 5.45 (1H, multiplet);
 5.58 (1H, doublet);
 5.90 (1H, broad singlet).

1-Pivaloyloxy-6-hydroxy-IsoMB-530B lactone

Nuclear Magnetic Resonance Spectrum $\delta$ppm:
 0.87 (3H, doublet);
 1.22 (9H, singlet);
 1.70 (3H, singlet);
 3.91 (1H, doublet);
 4.32 (1H, multiplet);
 4.61 (1H, multiplet);
 5.42 (1H, multiplet);
 5.55 (1H, doublet);
 5.87 (1H, broad multiplet).

1-Isobutyryloxy-6-hydroxy-IsoMB-530B lactone

Nuclear Magnetic Resonance Spectrum $\delta$ppm:
 0.87 (3H, doublet);
 1.11 (6H, doublet);
 1.71 (3H, singlet);
 3.93 (1H, doublet);
 4.32 (1H, multiplet);
 4.60 (1H, multiplet);
 5.44 (1H, multiplet);
 5.57 (1H, doublet);
 5.85 (1H, broad singlet).

1-Acetoxy-6-hydroxy-IsoMB-530B lactone

Nuclear Magnetic Resonance Spectrum $\delta$ppm:
 0.84 (3H, doublet);
 1.71 (3H, singlet);
 2.06 (3H, singlet);
 3.90 (1H, doublet);
 4.30 (1H, multiplet);
 4.66 (1H, multiplet);
 5.46 (1H, multiplet);
 5.53 (1H, multiplet);
 5.88 (1H, broad singlet).

1-Butyryloxy-6-hydroxy-IsoMB-530B lactone

Nuclear Magnetic Resonance Spectrum $\delta$ppm:
 0.83 (3H, doublet);
 0.98 (3H, triplet);
 1.72 (3H, singlet);
 3.87 (1H, doublet);
 4.34 (1H, multiplet);
 4.64 (1H, multiplet);
 5.43 (1H, doublet);
 5.54 (1H, doublet);
 5.91 (1H, broad singlet).

1-Isovaleryloxy-6-hydroxy-IsoMB-530B lactone

Nuclear Magnetic Resonance Spectrum $\delta$ppm:
 0.82 (6H, doublet);
 0.88 (3H, doublet);
 1.73 (3H, singlet);
 3.91 (1H, doublet);
 4.30 (1H, multiplet);
 4.65 (1H, multiplet);
 5.44 (1H, multiplet);
 5.54 (1H, doublet);
 5.90 (1H, broad singlet).

EXAMPLE 9

The procedure described in Example 1 was repeated, except that the MB-530B was replaced by the appropriate MB-530A 1-acylate to give the following compounds (nuclear magnetic resonance spectra were measured at 90 MHz in deuterochloroform, using tetramethylsilane as the internal standard):

Methyl 1-(2,2-dimethylbutyryloxy)-3-hydroxy-MB-530B carboxylate

Nuclear Magnetic Resonance Spectrum $\delta$ppm:
 0.83 (3H, triplet);
 0.91 (3H, doublet);
 1.12 (6H, singlet);
 1.34 (3H, singlet);
 3.73 (3H, singlet);
 3.81 (1H, multiplet);
 4.26 (1H, quartet);
 5.45 (2H, multiplet);
 5.91 (1H, doubled doublet);
 6.01 (1H, doublet).

Methyl 1-pivaloyloxy-3-hydroxy-MB-530B carboxylate

Nuclear Magnetic Resonance Spectrum δppm:
0.90 (3H, doublet);
1.23 (9H, singlet);
1.33 (3H, singlet);
3.74 (3H, singlet);
3.82 (1H, multiplet);
4.25 (1H, quartet);
5.44 (2H, multiplet),
5.92 (1H, doubled doublet);
6.01 (1H, doublet).

Methyl 1-isobutyryloxy-3-hydroxy-MB-530B carboxylate

Nuclear Magnetic Resonance Spectrum δppm:
0.92 (3H, doublet);
1.10 (6H, doublet);
1.36 (3H, singlet);
3.73 (3H, singlet);
3.83 (1H, multiplet);
4.24 (1H, quartet),
5.43 (2H, multiplet);
5.91 (1H, doubled doublet);
6.00 (1H, doublet).

Methyl 1-acetoxy-3-hydroxy-MB-530B carboxylate

Nuclear Magnetic Resonance Spectrum δppm:
0.92 (3H, doublet);
1.38 (3H, singlet);
2.07 (3H, singlet);
3.74 (3H, singlet);
3.84 (1H, multiplet);
4.26 (1H, quartet);
5.45 (2H, multiplet);
5.91 (1H, doubled doublet);
6.03 (1H, doublet).

Methyl 1-butyryloxy-3-hydroxy-MB-530B carboxylate

Nuclear Magnetic Resonance Spectrum δppm:
0.90 (3H, doublet);
1.00 (3H, triplet);
1.36 (3H, singlet);
3.73 (3H, singlet);
3.85 (1H, multiplet);
4.26 (1H, quartet);
5.42 (2H, multiplet);
5.91 (1H, doubled doublet);
6.03 (1H, doublet).

Methyl 1-isovaleryloxy-3-hydroxy-MB-530B carboxylate

Nuclear Magnetic Resonance Spectrum δppm:
0.82 (6H, doublet);
0.92 (3H, doublet);
1.37 (3H, singlet);
3.73 (3H, singlet);
3.86 (1H, multiplet);
4.25 (1H, quartet);
5.43 (2H, multiplet);
5.92 (1H, doubled doublet);
6.02 (1H, doublet).

We claim:

1. A 1-acyloxy-6-hydroxy-IsoMB-530B lactone of the formula (I):

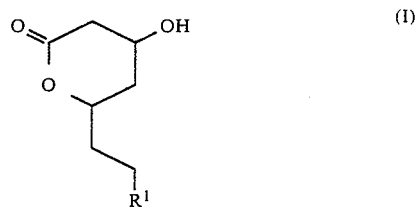

wherein $R^1$ represents a group of the formula

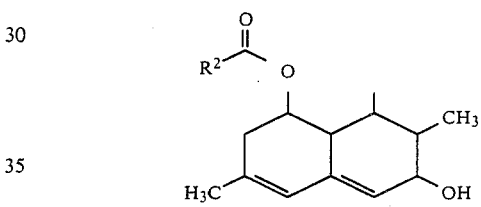

wherein $R^2$ is a $C_1$–$C_{10}$ alkyl group.

2. The lactone of claim 1, wherein $R^2$ represents an alkyl group selected from methyl, ethyl, propyl, butyl, pentyl, hexyl, heptyl, octyl, nonyl, decyl, isopropyl, isobutyl, sec-butyl, t-butyl, isopentyl, neopentyl, t-pentyl, isohexyl, 1-ethylpropyl, 1-methylpentyl, 1-ethyl-1-methylpropyl, 1,1-dimethylpentyl, 1,2-dimethylpentyl, 1-methylhexyl, 1,1-dimethylhexyl, 1-methylheptyl, 1,1-dimethylheptyl, 1-methyloctyl, 1,1-dimethyloctyl and 1-methylnonyl groups.

3. The lactone of claim 1, wherein $R^2$ represents a sec-butyl group.

* * * * *